(12) United States Patent
Chang et al.

(10) Patent No.: US 12,370,271 B2
(45) Date of Patent: Jul. 29, 2025

(54) GADOLINIUM-BASED COMPOUND, PREPARATION METHOD THEREFOR, AND MRI CONTRAST AGENT CONTAINING SAME

(71) Applicant: KYUNGPOOK NATIONAL UNIVERSITY INDUSTRY-ACADEMIC COOPERATION FOUNDATION, Busan (KR)

(72) Inventors: Yong Min Chang, Daegu (KR); Md Kamrul Islam, Daegu (KR)

(73) Assignee: KYUNGPOOK NATIONAL UNIVERSITY INDUSTRY-ACADEMIC COOPERATION FOUNDATION, Busan (KR)

( * ) Notice: Subject to any disclaimer, the term of this patent is extended or adjusted under 35 U.S.C. 154(b) by 607 days.

(21) Appl. No.: 17/794,807

(22) PCT Filed: Jan. 22, 2021

(86) PCT No.: PCT/KR2021/000894
§ 371 (c)(1),
(2) Date: Jul. 22, 2022

(87) PCT Pub. No.: WO2021/150052
PCT Pub. Date: Jul. 29, 2021

(65) Prior Publication Data
US 2023/0094602 A1    Mar. 30, 2023

(30) Foreign Application Priority Data

Jan. 22, 2020   (KR) .................. 10-2020-0008883
Jan. 22, 2021   (KR) .................. 10-2021-0009134

(51) Int. Cl.
*A61K 49/08*   (2006.01)
*A61K 49/10*   (2006.01)

(52) U.S. Cl.
CPC .......... *A61K 49/085* (2013.01); *A61K 49/108* (2013.01)

(58) Field of Classification Search
CPC ......................... A61K 49/108; A61K 49/085
See application file for complete search history.

(56) References Cited

U.S. PATENT DOCUMENTS

| 2002/0127629 | A1 | 9/2002 | Bogdanov et al. |
| 2016/0251378 | A1 | 9/2016 | Schmitthenner et al. |
| 2021/0188787 | A1* | 6/2021 | Ouerfelli ............. C07D 257/02 |

FOREIGN PATENT DOCUMENTS

KR    20190111356    10/2019

OTHER PUBLICATIONS

Bogdanov et al., "Oligomerization of paramagnetic substrates result in signal amplification and can be used for MR imaging of molecular targets." Molecular imaging 2002, vol. 1, No. 1, pp. 16-23.
Endres et al., "DNA-TiO2 nanoconjugates labeled with magnetic resonance contrast agents" Journal of the american chemical society 2007, vol. 129, No. 51, pp. 15760-15761.
International Search Report and Written Opinion issued in Corresponding PCT Application No. PCT/KR2021/000894, dated Apr. 30, 2021 (English Translation provided).

* cited by examiner

*Primary Examiner* — James W Rogers
(74) *Attorney, Agent, or Firm* — NORTON ROSE FULBRIGHT US LLP

(57) ABSTRACT

The present invention relates to a novel gadolinium-based compound having a structure in which a gadolinium complex and ferulic acid are linked via a linker, a preparation method therefor, and an MRI contrast agent containing same.

10 Claims, 9 Drawing Sheets

GADOLINIUM-BASED COMPOUND, PREPARATION METHOD THEREFOR, AND MRI CONTRAST AGENT CONTAINING SAME

CROSS-REFERENCE TO RELATED APPLICATIONS

This application a national phase under 35 U.S.C. § 371 of International Application No. PCT/KR2021/000894 filed Jan. 22, 2021, which claims priority to KR Patent Application No. 10-2020-0008883 filed Jan. 22, 2020 and KR Patent Application No. 10-2021-0009134 filed Jan. 22, 2021. The contents of each of the referenced applications are incorporated into the present application by reference.

TECHNICAL FIELD

The present disclosure relates to a novel gadolinium-based compound, a method for preparation of the same, and an MRI contrast agent containing the same. Specifically, the present disclosure relates to a novel gadolinium-based compound having a structure in which a gadolinium complex and a ferulic acid are bonded to each other via a linking group, a method for preparing the same, and an MRI contrast agent containing the same.

DESCRIPTION OF RELATED ART

Today, the number of patients with degenerative brain disease is increasing due to the aging of the population. Accordingly, the need for early detection of the disease is emerging. Degenerative brain diseases include Parkinson's disease, vascular dementia, Alzheimer's disease, and the like. Neurotoxicity due to excessive accumulation of amyloid beta polymer (oligomeric Aβ) is considered as one of the causes of the disease.

The amyloid beta (Aβ) is a major component of amyloid plaque found in a brain of an Alzheimer's patient, and refers to 36 to 43 amino acid peptides that are critically involved in the Alzheimer's disease. The peptide is derived from amyloid precursor protein (APP).

The amyloid beta molecules may aggregate with each other to form a soluble polymer that may exist in several forms. It is known that the formed amyloid beta polymer (oligomeric Aβ) is toxic to nerve cells, and excessive accumulation in the brain thereof is directly involved in the pathogenesis of Alzheimer's disease. Therefore, it was expected that sensing change in a concentration of the amyloid beta polymer would enable early diagnosis of the degenerative brain diseases.

Magnetic Resonance Image (MRI) refers to a method of obtaining anatomical, physiological, and biochemical information images of the body using a phenomenon in which the distributions of hydrogen atoms in different tissues of the body are different from each other and the hydrogen atoms are relaxed in a magnetic field. Unlike CT or PET, MRI does not use radiation harmful to the human body and creates images inside the body using the gradient of the magnetic field and radio waves under a strong magnetic field. Thus, the MRI is non-invasive, has high resolution, and has excellent soft tissue examination capabilities.

In order to use the MRI equipment more precisely, a contrast agent is injected into a subject to obtain an MRI image. The contrast between tissues on the MRI image is a phenomenon that occurs because the relaxation actions in which the nuclear spins of water molecules to return to the equilibrium state in the different tissues are different from each other. The contrast agent uses a paramagnetic or superparamagnetic material to affect the relaxation action to enhance the difference in relaxation between tissues and thus induce change in the MM signal to make the contrast between the tissues clearer.

Currently, the most commonly used contrast agent in clinical practice is a contrast agent based on gadolinium (Gd) chelate. Currently, Gd-DTPA (Magnevist®), Gd-DOTA (Dotaram®), Gd(DTPA-BMA) (Omniscan®), Gd(DO3A-HP) (ProHance®), Gd(BOPTA) (MultiHance®), etc. are being used. However, most of the commercially available contrast agents are non-specific contrast agents distributed in the extracellular fluid (ECF). Only a liver-specific contrast agent is used as a specific contrast agent. Recent research is related to the development of a contrast agent that has a specific target or that may exhibit signal enhancement due to physiological activity (pH change, enzyme activity). Currently, sufficient results about MRI contrast agents specific to degenerative brain diseases have not been obtained.

DISCLOSURE

Technical Purpose

One purpose of the present disclosure is to provide a gadolinium-based compound that may be used as an MRI contrast material and, in particular, has specificity to degenerative brain disease.

Another purpose of the present disclosure is to provide an MRI contrast agent containing the compound.

Another purpose of the present disclosure is to provide a method for preparation of the compound.

Technical Solution

According to the present disclosure, there is provided a gadolinium-based compound represented by a following Chemical Formula 1:

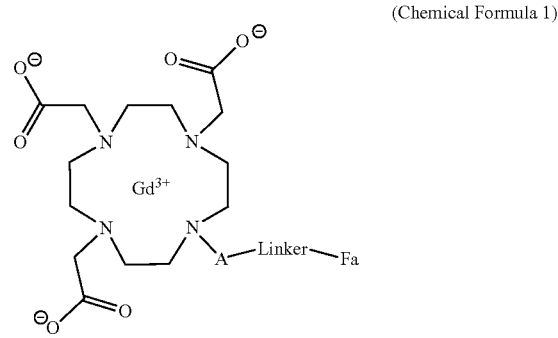

(Chemical Formula 1)

In the above Chemical Formula 1, A represents *—$(CH_2)_n$-$A^1$-*, n represents any integer from 0 to 5, $A^1$ represents *—COO—*, *—CO—*, *—NH—*, *—$CH_2$—*, *—CONH—*, or *—O—*, Linker represents *-$L^1$-NHCO-$L^2$-*, *-$L^1$-O—R—O-$L^2$-*, *-$L^1$-$CH_2$-$L^2$-*, *-$L^1$-NH-$L^2$-*, or *-$L^1$-COO-$L^2$-* , $L^1$ represents linear or branched (C1-C30)alkyl, $L^2$ represents a single bond, hydrogen or linear or branched (C1-C30)alkyl, R represents linear or branched (C1-C20)alkyl, Fa represents a following Chemical Formula 2:

(Chemical Formula 2)

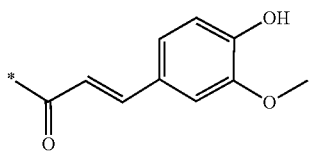

* indicates a connection site.

Further, according to the present disclosure, an MRI contrast agent containing the gadolinium-based compound represented by the Chemical Formula 1 is provided.

Further, according to the present disclosure, there is provided a method for preparing the gadolinium-based compound represented by the Chemical Formula 1, the method comprising following steps:

(a) reacting a compound represented by a following Chemical Formula 1-1 with a following Chemical Formula 1-2 to obtain a following Chemical Formula 1-3:

(Chemical Formula 1-1)

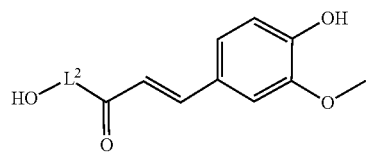

wherein in the Chemical Formula 1-1, $L^2$ is the same as previously defined in the Chemical Formula 1, (Chemical Formula 1-2)

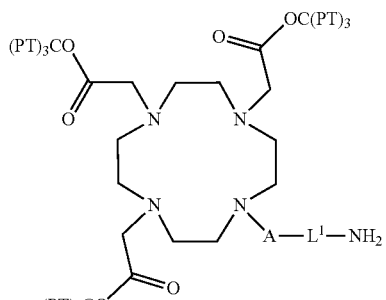

(Chemical Formula 1-3)

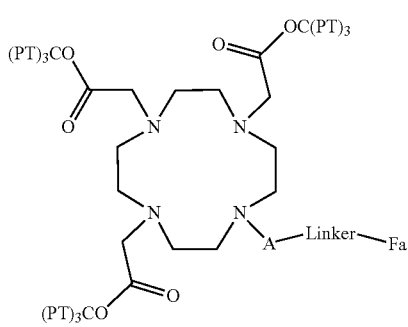

wherein in each of the Chemical Formulas 1-2 and 1-3, PT represents a protecting group, Linker represents *-$L^1$-NH-$L^2$-*, each of $L^1$, $L^2$, A, and Fa is as previously defined in the Chemical Formula 1;

(b) removing the protecting group PT from the compound of the Chemical Formula 1-3; and (c) reacting a compound obtained in the step (b) with gadolinium hydrate to obtain the compound of the Chemical Formula 1.

Technical Effects

The novel gadolinium-based compound according to the present disclosure not only has sufficient self-relaxation properties to be used as an MRI contrast material, but also binds to amyloid beta polymer (oligomeric Aβ), so that the compound has an MRI contrast enhancing effect in the presence of the amyloid beta polymer (oligomeric Aβ), and thus may be used for diagnosis of diseases related to the amyloid beta polymer (oligomeric Aβ), specifically, the degenerative brain disease.

DETAILED DESCRIPTIONS

Figure 1A:
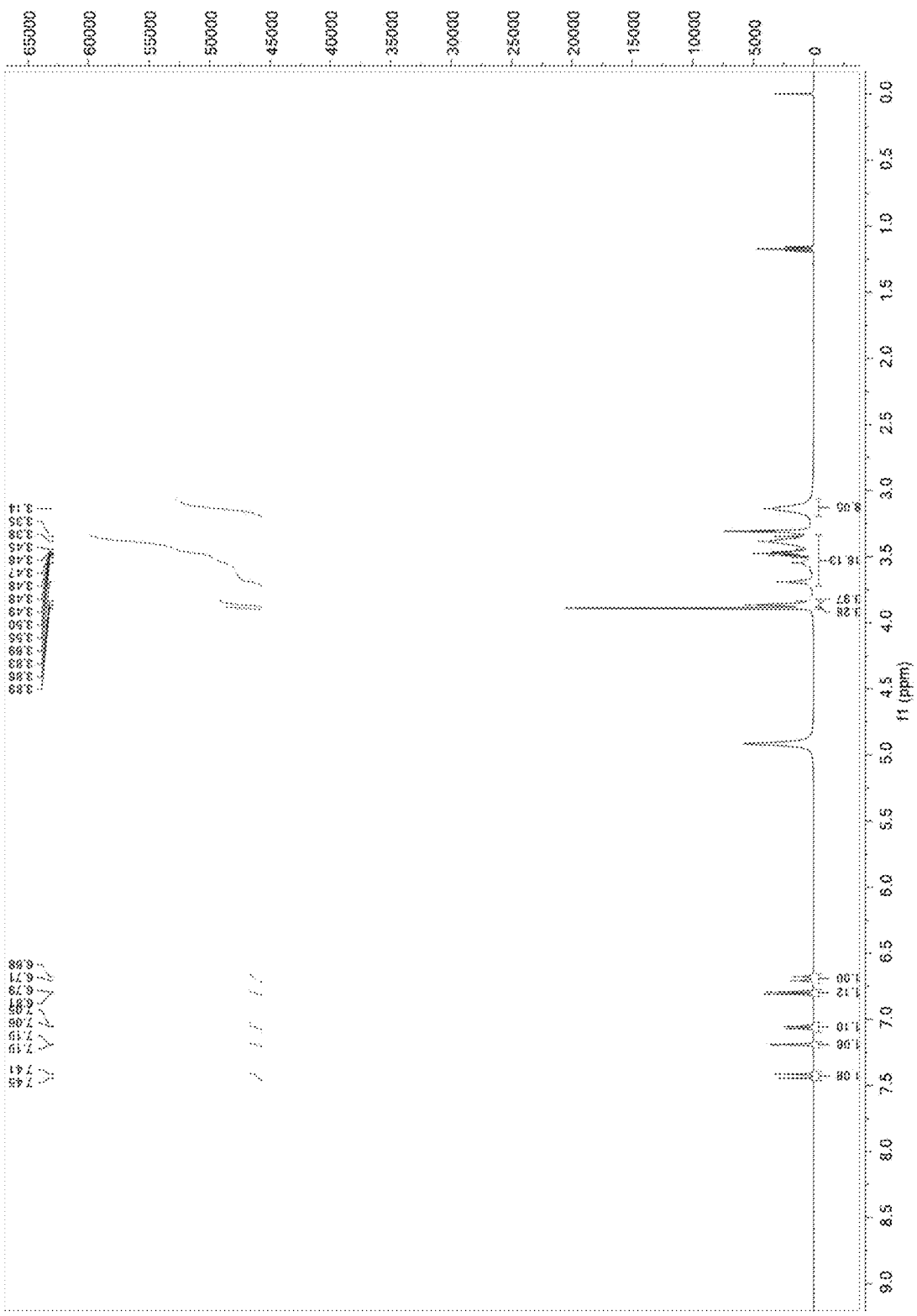
FIG. 1A is a $^1$H NMR spectrum of a compound L prepared in Preparation Example of a compound according to the present disclosure.
Figure 1B:
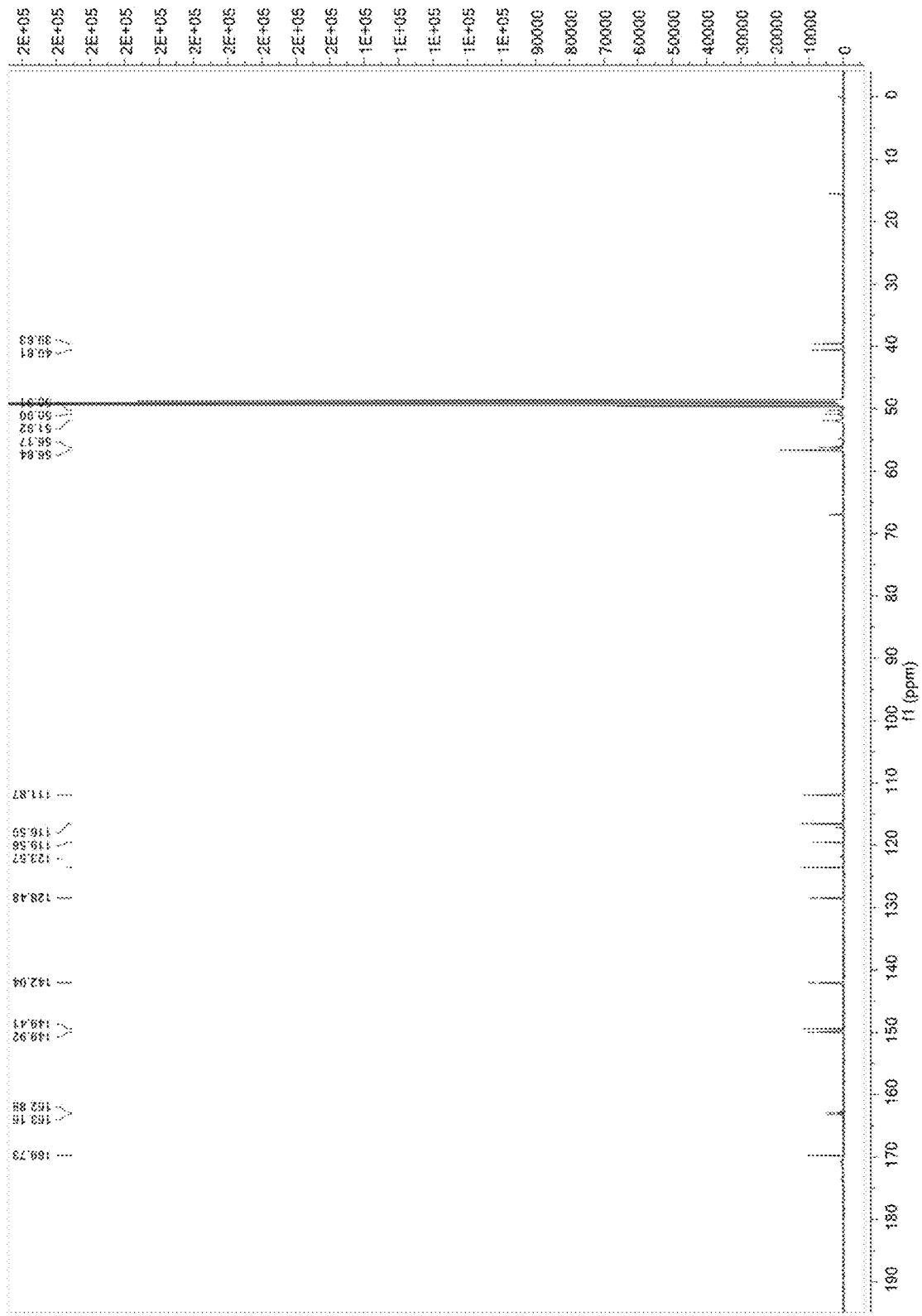
FIG. 1B is a $^{13}$C NMR spectrum of the compound L prepared in Preparation Example of a compound according to the present disclosure.
Figure 1C:
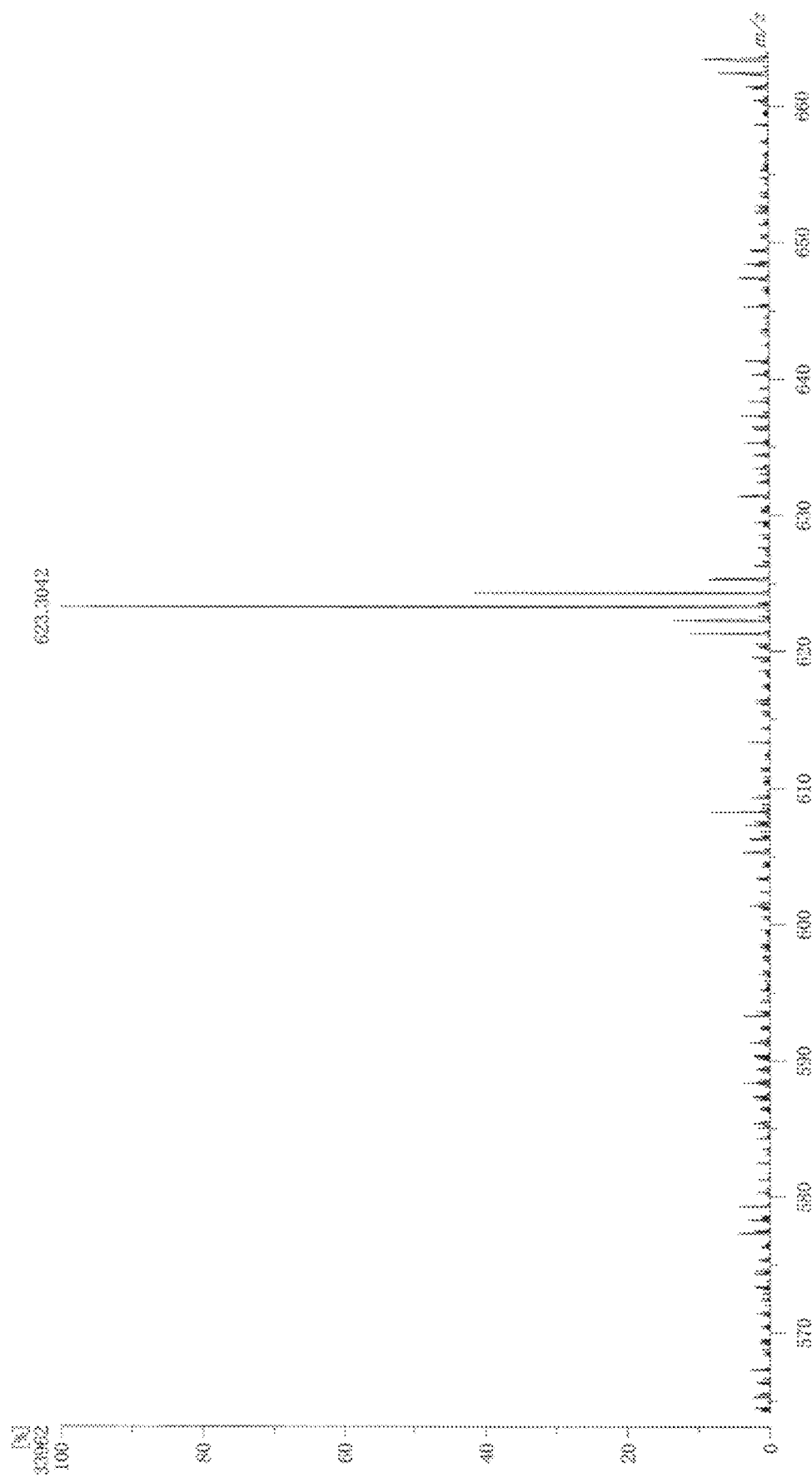
FIG. 1C is an HR-MS spectrum of the compound L prepared in Preparation Example of a compound according to the present disclosure.
Figure 1D:
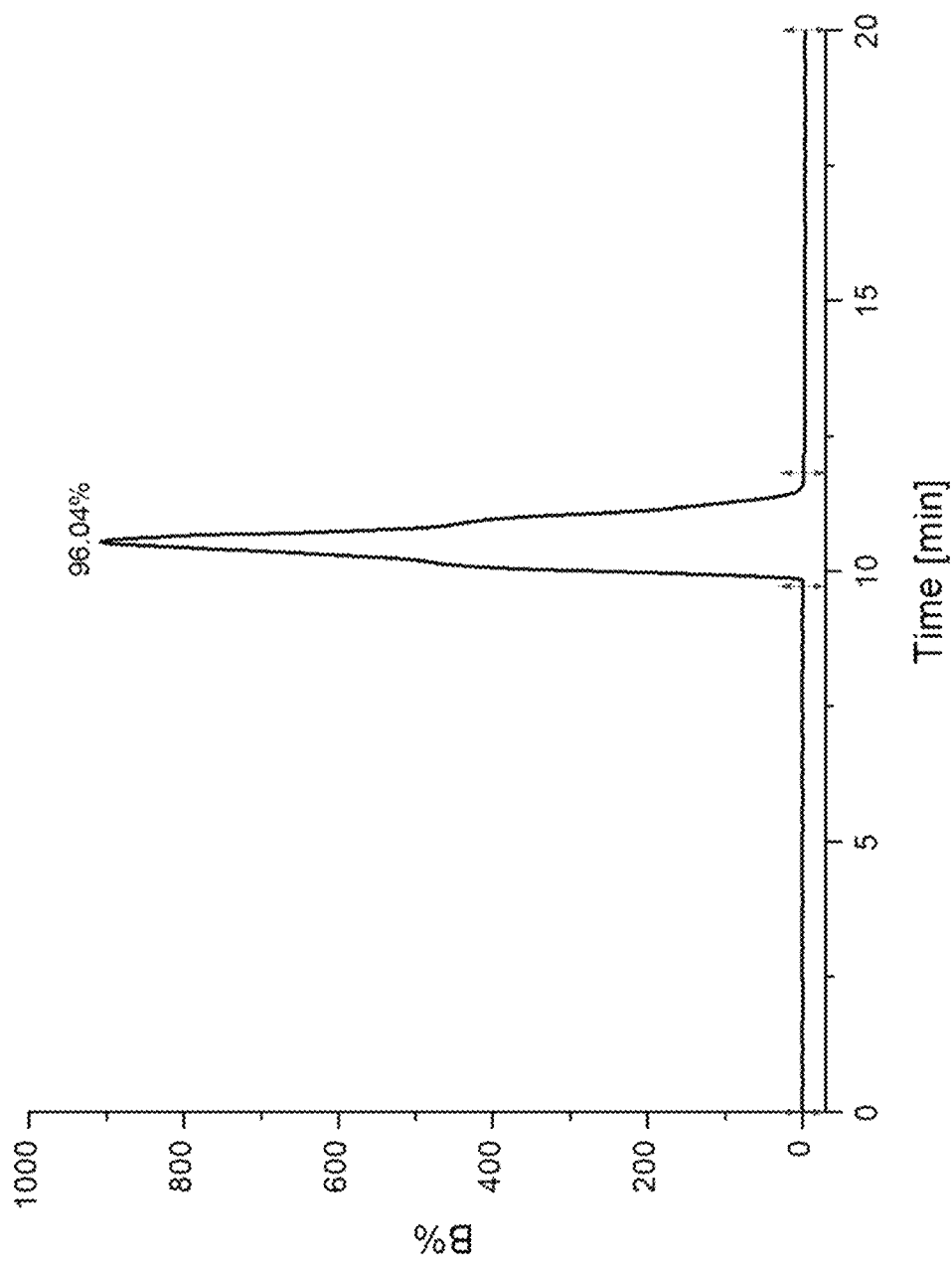
FIG. 1D is an HPLC chromatogram of the compound L prepared in Preparation Example of a compound according to the present disclosure.

The terminology used herein is for the purpose of describing particular embodiments only and is not intended to be limiting of the present disclosure. Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A gadolinium-based compound according to the present disclosure may be represented by a following Chemical Formula 1:

(Chemical Formula 1)

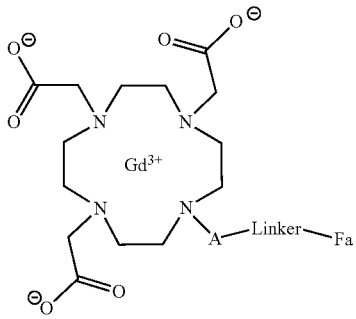

In the above Chemical Formula 1, A represents *—(CH$_2$)$_n$-A$^1$-*, n may represent any integer from 0 to 5, specifically any integer from 1 to 5, and more specifically, any integer from 1 to 3, A$^1$ represents *—COO—*, *—CO—*, *—NH—*, *—CH$_2$—*, *—CONH—*, or *—O—*, Linker represents *-L$^1$-NHCO-L$^2$-*, *-L$^1$-O—R—O-L$^2$-*, *-L$^1$-CH$_2$-L$^2$-*, *-L$^1$-NH-L$^2$-*, or *-L$^1$-COO-L$^2$-*, specifically, *-L$^1$-CH$_2$-L$^2$-*, L$^1$ represents linear or branched (C1-C30)alkyl, specifically, linear or branched (C1-C10)alkyl, more specifically, linear or branched (C1-C5)alkyl, L$^2$ represents a single bond, hydrogen or linear or branched (C1-C30)alkyl, specifically, a singe bond, R represents linear or branched (C 1-C20)alkyl, specifically, linear or branched (C1-C10)alkyl, more specifically, linear or branched (C1-C5)alkyl, Fa represents a following Chemical Formula 2:

(Chemical Formula 2)

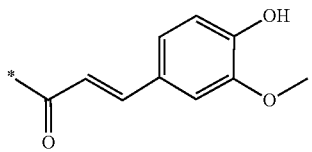

* indicates a connection site.

According to one embodiment of the present disclosure, in the Chemical Formula 1, n may represent any integer from 1 to 5, and A$^1$ may represent *—CONH—*.

According to another embodiment of the present disclosure, L$^1$ may represent linear or branched (C1-C10)alkyl, and L$^2$ may represent the single bond.

In the gadolinium-based compound of the Chemical Formula 1, gadolinium may be coordinated with at least one water molecule. For example, in the gadolinium-based compound of the Chemical Formula 1, gadolinium may coordinate with one or two water molecules.

In the gadolinium-based compound of the Chemical Formula 1 of the present disclosure, when A$^1$ is *—COO—*, *—CO—*, or *—CONH—*, an oxygen atom may form a coordination bond with gadolinium.

The Chemical Formula 2 of the present disclosure is a portion derived from a ferulic acid. The ferulic acid is a phenolic chemical found in a cell wall of a plant. It is reported that the ferulic acid has high antioxidant power against various reactive oxygen species derived from oxygen molecules, and exhibits a strong antioxidant effect against oxidative transition metals such as iron ions and copper ions. Thus, the ferulic acid has been used as a major component of anti-aging agents and disease-treatment agents for diseases because of its antioxidant effect. However, the use of the ferulic acid for an MRI contrast agent with a targeting function toward amyloid beta polymer (oligomeric Aβ) has not been considered until now.

The gadolinium-based compound of the Chemical Formula 1 of the present disclosure may specifically bind to mammalian amyloid beta polymer (oligomeric Aβ), as shown in Examples to be described later.

Further, the compound according to the present disclosure is water-soluble and coordinates with at least one or more water molecules and thus has magnetic-relaxation properties. Thus, the compound increases the relaxation of at least one or more water molecules and hydrogen atoms in the human body to improve the image contrast, and thus may be used as an MRI contrast material.

Accordingly, according to the present disclosure, an MRI contrast agent containing a gadolinium-based compound represented by the Chemical Formula 1 is provided. Further, since the compound according to the present disclosure is capable of binding to the amyloid beta polymer (oligomeric Aβ), the Mill contrast agent according to the present disclosure may be used to diagnose a disease associated with amyloid beta polymer (oligomeric Aβ), more specifically, degenerative brain diseases such as Parkinson's disease, vascular dementia, Alzheimer's disease. Accordingly, according to one embodiment of the present disclosure, a specific MRI contrast agent for diagnosing degenerative brain disease containing the compound of the Chemical Formula 1 may be provided. Moreover, as described above, according to a recent study, the amyloid beta polymer (oligomeric Aβ) induced by amyloid precursor protein is excessively accumulated in the brain and thus was involved in onset of Alzheimer's disease. Therefore, an MRI contrast agent containing the compound according to the present disclosure targeting the amyloid beta polymer (oligomeric Aβ) may act as a specific MRI contrast agent for the diagnosis of Alzheimer's disease, especially for early diagnosis thereof.

Further, according to one embodiment of the present disclosure, there is provided a method for preparing the gadolinium-based compound represented by the Chemical Formula 1, the method comprising following steps:

(a) reacting a compound represented by a following Chemical Formula 1-1 with a following Chemical Formula 1-2 to obtain a following Chemical Formula 1-3:

(Chemical Formula 1-1)

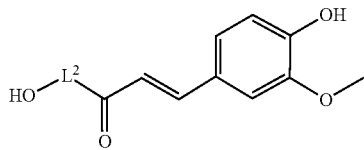

wherein in the Chemical Formula 1-1, $L^2$ is the same as previously defined in the Chemical Formula 1,

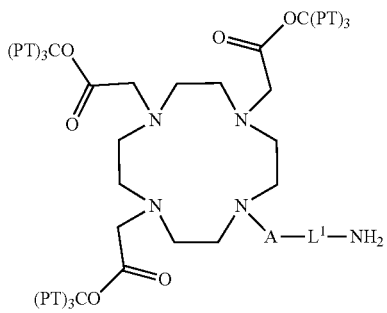

(Chemical Formula 1-2)

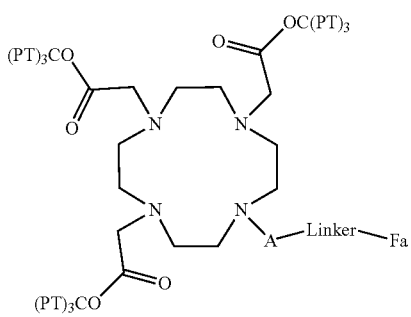

(Chemical Formula 1-3)

wherein in each of the Chemical Formulas 1-2 and 1-3, PT represents a protecting group, Linker represents *-$L^1$-NH-$L^2$-*, each of $L^1$, $L^2$, A, and Fa is as previously defined in the Chemical Formula 1;

(b) removing the protecting group PT from the compound of the Chemical Formula 1-3; and (c) reacting a compound obtained in the step (b) with gadolinium hydrate to obtain the compound of the Chemical Formula 1.

According to one embodiment of the present disclosure, in the step (a), $L^2$ may be a single bond.

If necessary, before performing the step (a), the —OH group directly linked to a benzene ring in the Chemical Formula 1-1 may be protected using a protecting group commonly used for the —OH group, for example, acetyl, benzoyl, methoxymethyl ether, methyl thiomethyl ether, etc. After the protection of the —OH group, the step (a) may be performed. In addition, if necessary, before performing the step (a), the —OH group directly connected to $L_2$ in the Chemical Formula 1-1 may be substituted with a halogen using a halogen compound. After the halogenation, the step (a) may be performed.

In the above Chemical Formulas 1-2 and 1-3, PT may represent a protecting group, which may include a protecting group commonly used for protecting a —COOH group, for example, methyl, benzyl, tert-butyl, or the like.

The step (b) refers to a step for removing the protecting group, where the protecting group, that is, PT may be removed using a method commonly used in the art, for example, using an aqueous base or an aqueous acid.

Hereinafter, for a detailed understanding of the present disclosure, the compound according to the present disclosure, the method for preparing the same, and characteristics of the MRI contrast agent containing the same will be described based on a representative compound according to the present disclosure.

1. Preparation Example of Compound According to the Present Disclosure

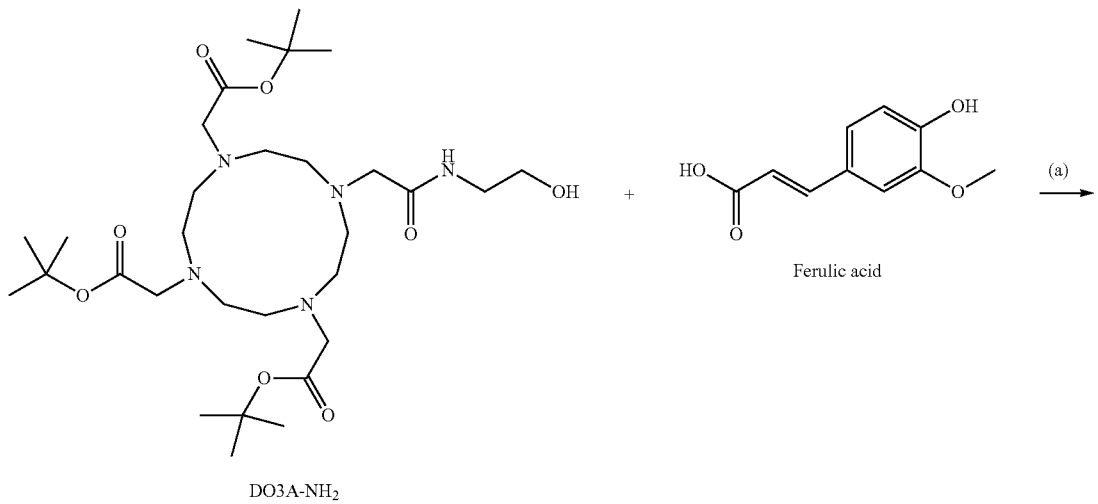

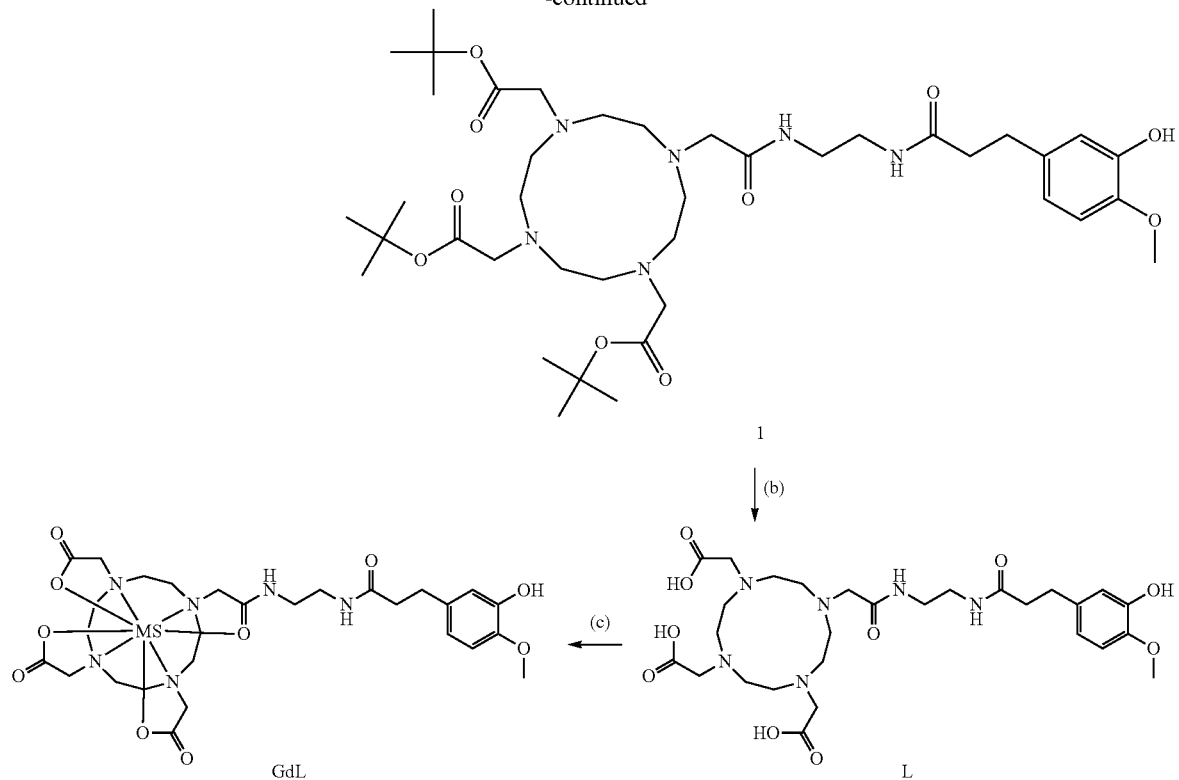

1) Synthesis of tri-tert-butyl 2,2',2"-(10-(2-((2-(3 -(3 -hydroxy-4-methoxyphenyl)acrylamido)ethyl)amino)-2-oxoethyl)-1,4,7,10-tetraazacyclododecane-1,4,7-triyl)(E)-triacetate (Compound 1).

Ferulic acid (0.2 g, 1.03 mmol), N,N-diisopropylethylamine (0.26 mL, 2.06 mmol) and hydroxybenzotriazole (HOBt) (0.24 g, 1.54 mmol) were dissolved in dimethylformamide (DMF)) (10 mL) to produce a mixed solution. Then, the mixed solution was stirred for 30 mins.

Then, 2-(1H-benzotriazol-1-yl)-1,1,3,3 -tetramethyluronium hexafluorophosphate (HBTU) (0.78 g, 2.06 mmol) and DO3A-NH$_2$ (0.64 g, 1.03 mmol) were added to the mixed solution and then the mixed solution was stirred at room temperature for 20 hours.

A reaction was stopped by addition of 10% sodium hydrogen carbonate thereto. Then, a resulting product was subjected to extraction with ethyl acetate (3×50 mL). A thus-obtained organic layer was washed with brine solution, and then sodium sulfate was added thereto to remove remaining moisture therefrom. Then, a resulting product was dried under vacuum to obtain an oily substance (Compound 1). (Yield: 0.72 g (89%))

An analysis result of HR-FAB-MS of the obtained Compound 1 is as follows.

HR-FAB-MS calculated for $C_{40}H_{66}N_6NaO_{10}$ (m/z): 813.4738 [M+Na]$^+$; found, 813.4743 [M+Na]$^+$ 2) Synthesis of (E)-2,2',2"-(10-(2-((2-(3 -(3 -hydroxy-4-methoxyphenyl)acrylamido)ethyl)amino)-2-oxoethyl)-1,4,7,10-tetraazacyclododecane-1,4,7-triyl)triacetic acid (compound L)

The compound 1 (0.7 g, 0.89 mmol) was dissolved in a mixture of trifluoroacetic acid (TFA) and dichloromethane (CH$_2$Cl$_2$) in an ice-bath to produce a mixed solution. Then, the mixed solution was stirred at room temperature until it was completely dissolved and became a clear solution. At this time, a reaction of the reactants was identified using TLC. After the reaction was sufficiently completed, the solvent was removed therefrom, and ethyl ether was added thereto to obtain a precipitate. Thereafter, the precipitate was filtered using a filter, and a filtrate was washed several times with ethyl ether, and dried in vacuum to obtain a pale yellowish-white solid (Compound L).

$^1$H NMR spectrum, $^{13}$C NMR spectrum, HR-MS spectrum and HPLC chromatogram of the obtained compound L are shown in FIGS. 1A to 1D, respectively.

(Yield: 0.48 g (87%))$^1$H NMR (500 MHz, MeOD); δ=7.43 (d, J=15.7 Hz, 1H), 7.19 (d, J=1.6 Hz, 1H), 7.06 (dd, J=8.2, 1.7 Hz, 1H), 6.80 (d, J=8.2 Hz, 1H), 6.69 (d, J=15.7 Hz, 1H), 3.89 (s, 3H), 3.88-3.82 (m, 4H), 3.72-3.34 (m, 16H), 3.20-3.06 (m, 8H).

$^{13}$C NMR (126 MHz, MeOD); δ=169.73, 163.16, 162.88, 149.92, 149.41, 142.04, 128.48, 123.57, 119.56, 116.59, 111.87, 56.64, 56.17, 51.92, 50.90, 50.31, 40.61, 39.63.

HR-MS calculated for $C_{28}H_{43}N_6O_{10}$(m/z): 623.3041 [M+H]$^+$; found, 623.3042 [M+H]$^+$ Purity analysis using analytical HPLC: 96.04%.

3) Synthesis of Compound GdL (compound according to the present disclosure)

The Compound L (0.4 g, 0.64 mmol) was dissolved in distilled water (10 mL) to produce a mixed solution, and then pH of the mixed solution was adjusted to pH 7 using 1M sodium hydroxide solution. Then, a further mixed solution in which Gd(Cl)$_3$·H$_2$O (0.24 g, 0.64 mmol) was dissolved in distilled water (5 mL) was added thereto. Thereafter, the mixed solution was stirred at room temperature for one day. At this time, pH of the solution was maintained in a range of 7 to 7.3 during the stirring. After completion of the stirring, a resulting product was filter using a filter and then a filtrate was further purified using high performance liquid chromatography (HPLC) to obtain the Compound GdL.

Figure 2A:
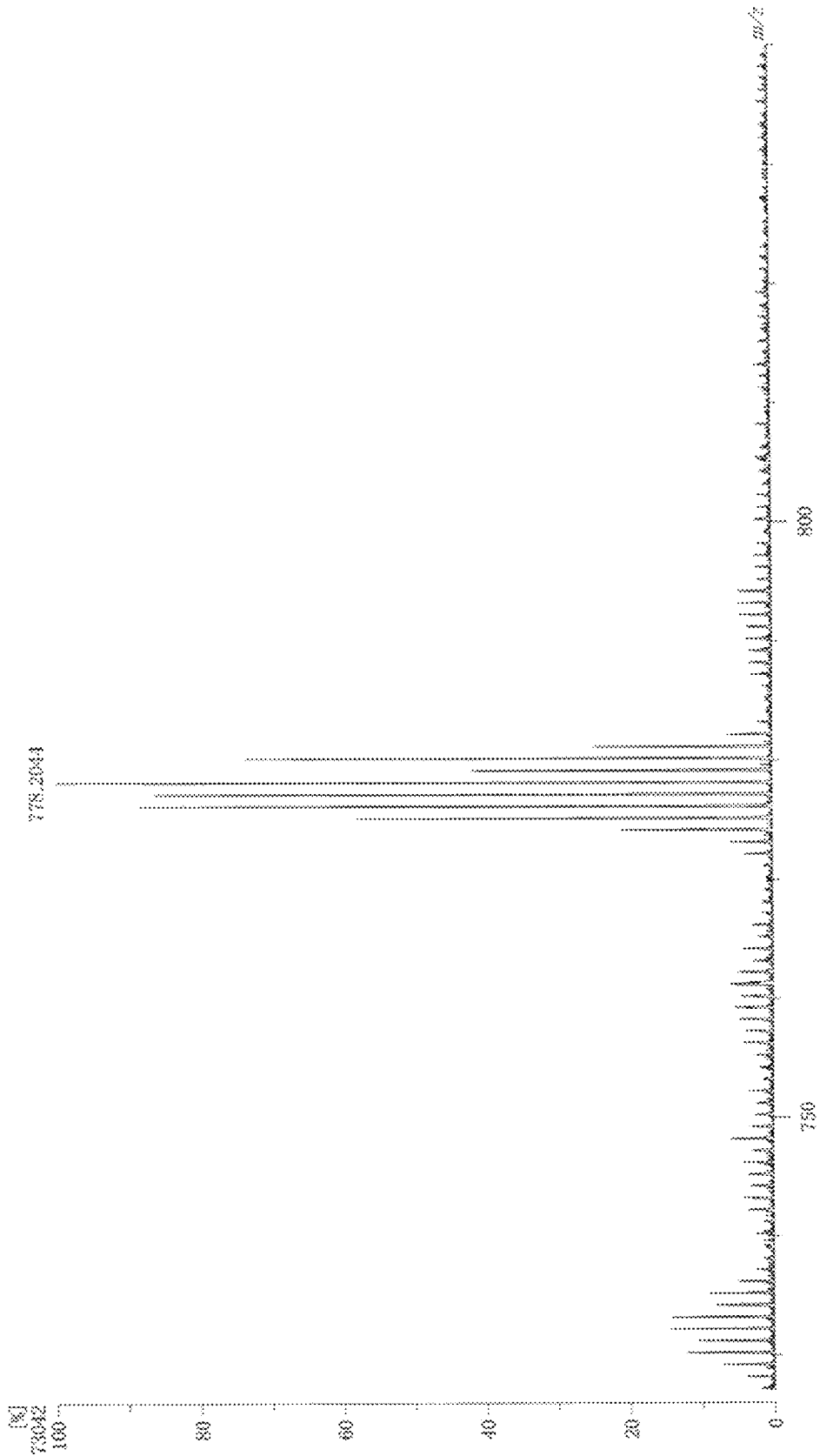
FIG. 2A is a HR-MS spectrum of GdL prepared in Preparation Example of a compound according to the present disclosure.
Figure 2B:
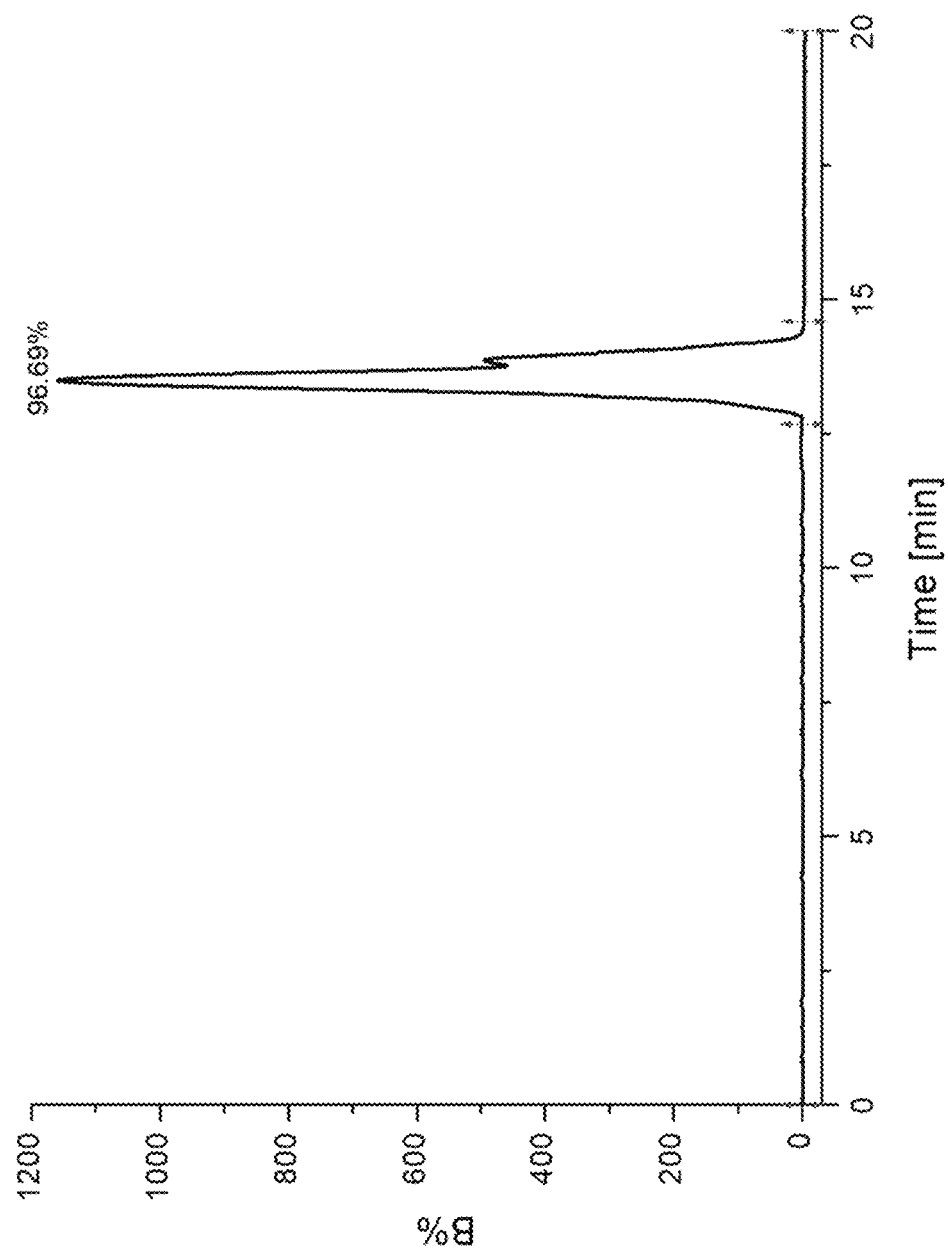
FIG. 2B is an HPLC chromatogram of GdL prepared in Preparation Example of a compound according to the present disclosure.

HR-MS spectrum and HPLC chromatogram of the obtained Compound GdL are shown in FIGS. 2A and 2B, respectively. (Yield: 0.15 g (31%))

HR-MS calculated for $C_{28}H_{40}GdN_6O_{10}$ (m/z): 778.2047 $[M+H]^+$; found, 778.2044 $[M+H]^+$ Purity analysis using analytical HPLC: 96.69%.

Hereinafter, characteristic evaluation of the prepared representative compound of the present disclosure was performed to determine whether the prepared representative compound of the present disclosure can be used as an MRI contrast material, and at the same time, has a targeting ability towards the amyloid beta polymer.

2. Methods and Results of Characteristic Evaluation of Compound According to the Present Disclosure 1) Measurement of Relaxivity A phantom was prepared by diluting the Compound GdL obtained using the above method to various concentrations (0.0625, 0.125, 0.25, 0.5, 1 mM) using tertiary distilled water, and then $T_1$ and $T_2$ relaxation times thereof were measured in 3T MRI. Thus, R (relaxivity=1/T) thereof at each of the concentrations was calculated and then the relaxivity ($r_1$ and $r_2$) of the Compound GdL obtained using the above method was calculated via linear regression analysis. (See FIG. 3)

Figure 3:
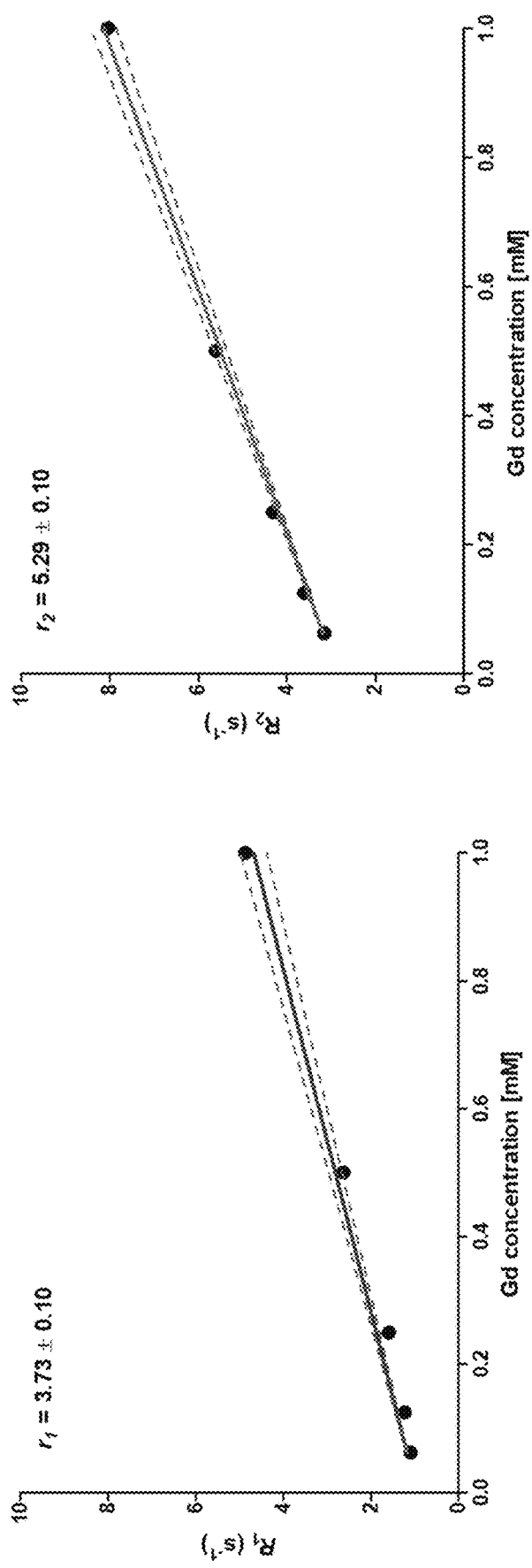
FIG. 3 shows an analysis graph of magnetic relaxivity ($r_1$, $r_2$) of GdL according to the present disclosure.

It was identified as shown in FIG. 3 that a $r_1$ value of GdL was measured to be 3.73±0.10, and a $r_2$ value thereof was measured to be 5.29±0.10. Thus, the contrast medium of the present disclosure exhibited sufficient relaxivity for clinical use. Thus, the Compound GdL obtained using the above method may be used as a MRI contrast agent.

2) Kinetic Stability Evaluation

Figure 4:
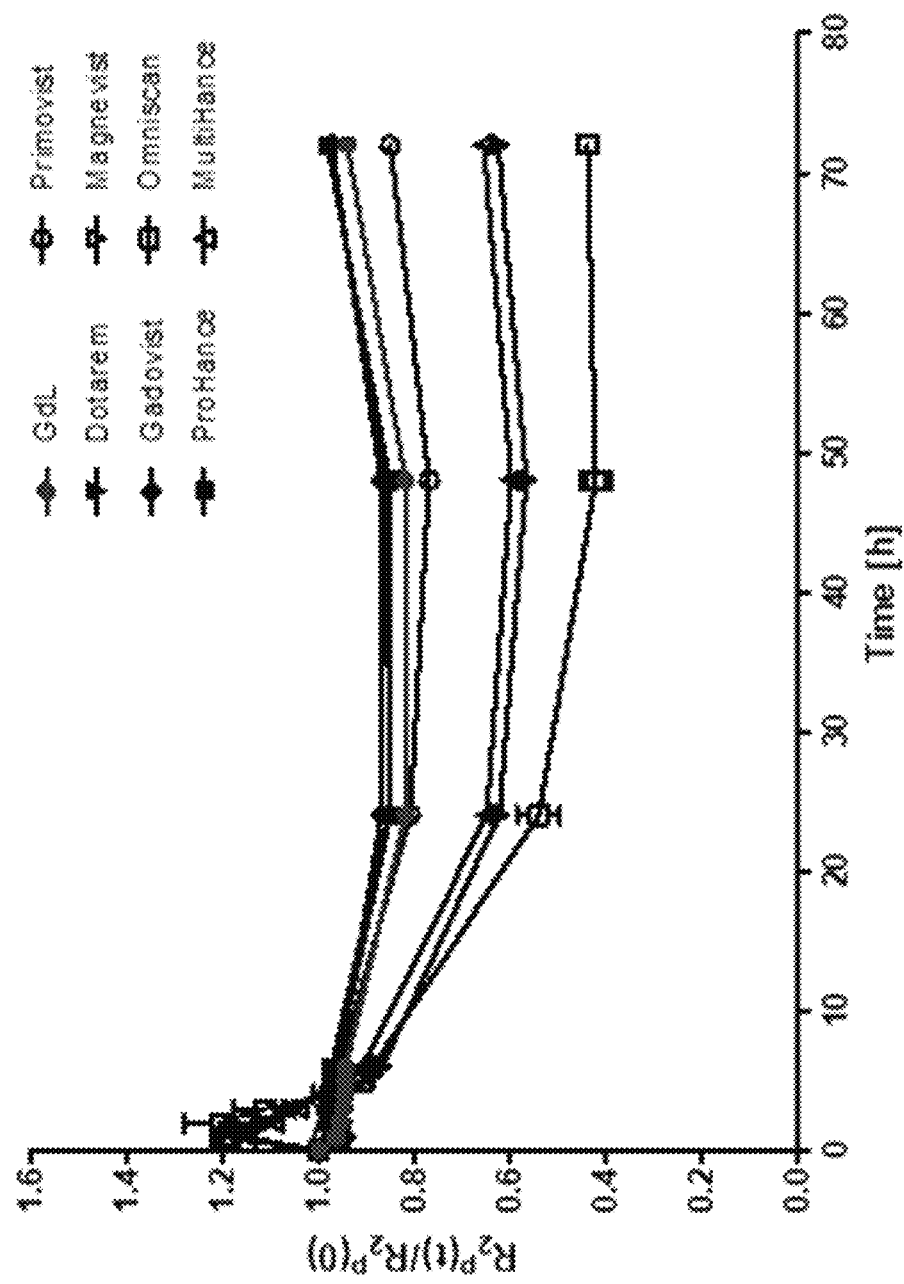
FIG. 4 shows a graph of kinetic stability of each of GdL according to the present disclosure and several commercial contrast agents (Gadovist, Dotarem, Prohance, Magnevist, Primovist, Omniscan, Multihance).

A phantom was prepared by diluting each of GdL and several commercial contrast agents (Gadovist, Dotarem, Prohance, Magnevist, Primovist, Omniscan, Multihance) to a concentration of 2.5 mM using PBS (pH 7.4), and then 250 mM of zinc chloride ($ZnCl_2$) was added, at 1 equivalent, thereto. Ligand-metal binding stability of the gadolinium complex was evaluated, and a result is shown in FIG. 4. This may be identified by measuring transmetallation of gadolinium ions due to zinc ions as a change in the relaxivity.

It is known that a gadolinium complex of a linear structure has relatively poor stability compared to that of a gadolinium complex of a cyclic structure. Referring to FIG. 4, it was identified that the synthesized GdL had higher stability than that of a linear contrast agent, and exhibited the change in the relaxivity similar to that of a cyclic commercial contrast agent, and thus had superior stability.

3) Phantom Test Method for Identification Whether Compound has Targeting Ability Toward Amyloid Beta Polymer HFIP (221.5 µl) was added to amyloid beta (1 mg, 1 mM) to produce a mixture which in turn was shaken for 1 hour at room temperature using a shaker to remove preaggregation.

Next, the amyloid beta from which the pre-aggregation was removed was dried in the air. Then, DMSO (221.5 µl) was added thereto to adjust a concentration thereof to 1 mM. Then, a suspension thereof was produced using a mixer and a sonicator, and PBS (1X, pH 7.4, 878.5 µl) was added to the suspension to adjust a concentration of the suspension to 0.2 mM.

Thereafter, the suspension was subjected to incubation for 4 days at 37° C. using a shaker. Then, amyloid beta polymer (oligomeric Aβ) that has been polymerized was dispensed by 200 µl. Then, a further mixed solution in which the Compound GdL was dissolved in PBS at a concentration of 2 mM was added thereto at 20 µl amount. A further mixed solution in which the commercial contrast agent (Gadovist®) was dissolved in PBS at a concentration of 2 mM was added thereto at 20 µl amount. Then, each of two resulting mixtures was incubated at 37° C. for 24 hours using a shaker.

After completion of the incubation, a supernatant was removed therefrom via centrifugation, and then the amyloid beta polymer was washed with PBS, and then 200 µl of PBS:DMSO=9:1 solution was added to a pellet thereof to prepare MRI phantom samples.

4) Experimental Results

Figure 5:
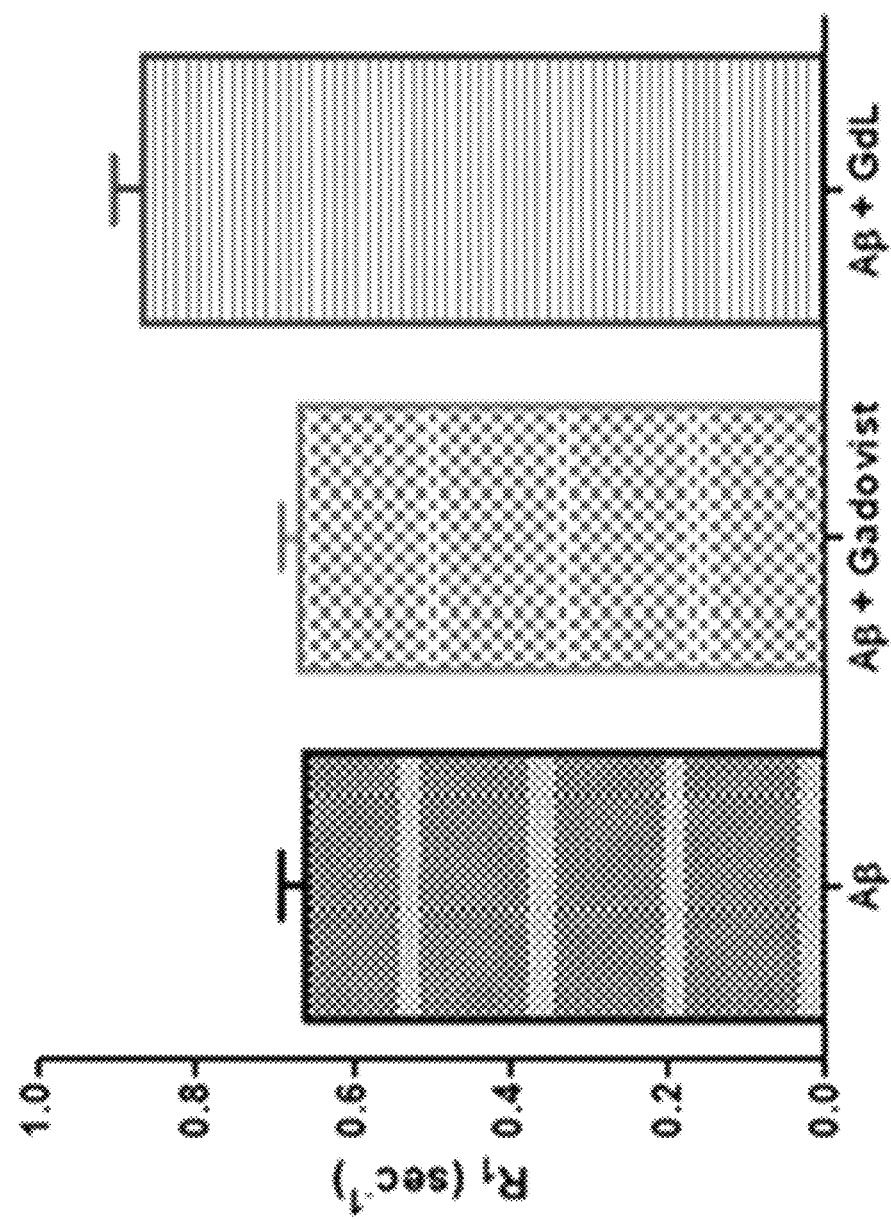
FIG. 5 shows a graph of a comparing result of MR signal intensities of MR $T_1$ phantoms of MRI phantom samples.

The amyloid beta polymer targeting ability test experiment was carried out in 9.4T MR equipment, and a result is shown in FIG. 5. FIG. 5 shows a graph of a comparing result of MR signal intensities of MR $T_1$ phantoms of the MRI phantom samples.

Referring to FIG. 5, a contrast enhancement effect of the phantom (control) incubated only with the amyloid beta polymer and a contrast enhancement effect of the phantom (comparative example) incubated with both of the commercial contrast medium (Gadovist®) and the amyloid beta polymer had no significant difference from each other. Thus, it was identified that the commercial contrast agent (Gadovist®) used as the comparative example had substantially no targeting effect toward the amyloid beta polymer.

On the contrary, the phantom incubated with GdL as the compound according to the present disclosure and the amyloid beta polymer exhibited a contrast enhancement effect that was significantly greater than that of each of the control and the comparative example using the commercial contrast medium (Gadovist®). Thus, it may be identified that the compound according to the present disclosure has a targeting effect toward amyloid beta polymer. Thus, it may be identified that the Compound GdL of the present disclosure is suitable as an amyloid beta polymer targeting contrast agent.

Although the above disclosure has been described with reference to a preferred embodiment of the present disclosure, those skilled in the art may variously modify the present disclosure within the scope not departing from the spirit and scope of the present disclosure described in the claims below.

What is claimed is:

1. A gadolinium-based compound represented by a following Chemical Formula 1:

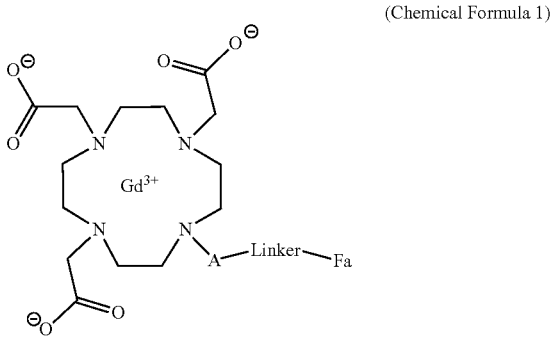

(Chemical Formula 1)

wherein in the Chemical Formula 1,
A represents *—$(CH_2)_n$-$A^1$-*,
n represents any integer from 0 to 5, A¹ represents *—COO—*, *—CO—*, *—NH—*, *—CH₂—*, *—CONH—*, or *—O—*, Linker represents *-L¹-NHCO-L²-*, *-L¹-O—R—O-L²-*, *-L¹-CH₂-L²-*, *-L¹-NH-L²-*, or *-L¹-COO-L²-*, L¹ represents linear or branched (C1-C30)alkyl, L² represents a single bond or linear or branched (C1-C30)alkyl, R represents linear or branched (C1-C20)alkyl, Fa represents a following Chemical Formula 2:

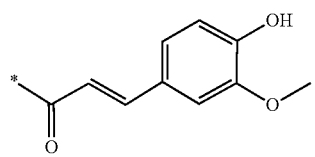

(Chemical Formula 2)

* indicates a connection site.

2. The gadolinium-based compound of claim 1, wherein n represents any integer from 1 to 5, and A¹ represents *—CONH—*.

3. The gadolinium-based compound of claim 1, wherein L¹ represents linear or branched (C1-C10)alkyl, and L² represents the single bond.

4. The gadolinium-based compound of claim 1, wherein the gadolinium coordinates with at least one water molecule.

5. The gadolinium-based compound of claim 1, wherein the compound specifically binds to mammalian amyloid beta polymer (oligomeric Aβ).

6. An MRI contrast agent comprising the gadolinium-based compound of claim 1.

7. The MRI contrast agent of claim 6, wherein the agent is used for diagnosis of a degenerative brain disease.

8. The MRI contrast agent of claim 7, wherein the agent is used for diagnosis of Alzheimer's disease.

9. A method for preparing a gadolinium-based compound, the method comprising the following steps:

(a) reacting a compound represented by the following Chemical Formula 1-1 with the following Chemical Formula 1-2 to obtain the following Chemical Formula 1-3:

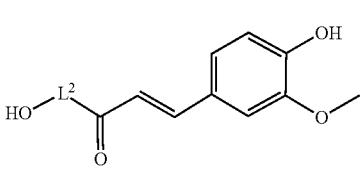

(Chemical Formula 1-1)

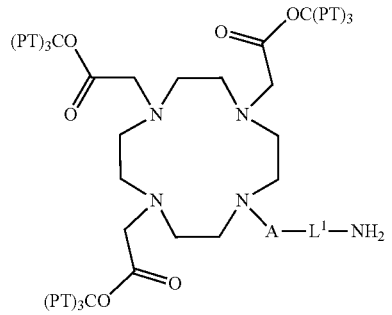

(Chemical Formula 1-2)

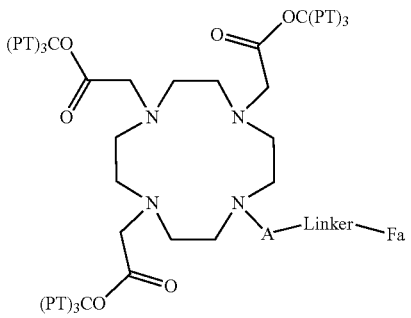

(Chemical Formula 1-3)

wherein in each of the Chemical Formulas 1-1, 1-2 and 1-3,

PT represents a protecting group,

A represents *—(CH₂)ₙ-A¹-*, n represents any integer from 0 to 5,

A¹ represents *—COO—*, *—CO—*, *—NH—*, *—CH₂—*, *—CONH—*, or *—O—*,

Linker represents *-L¹—NH-L²-*,

L¹ represents linear or branched (C1-C30)alkyl,

L² represents a single bond or linear or branched (C1-C30)alkyl,

Fa represents the following Chemical Formula 2:

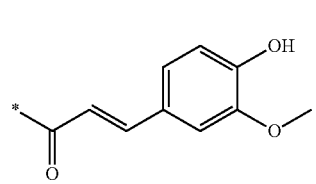

(Chemical Formula 2)

where * indicates a connection site, (b) removing the protecting group PT from the compound of the Chemical Formula 1-3; and (c) reacting a compound obtained in the step (b) with gadolinium hydrate to obtain the compound of the Chemical Formula 1:

(Chemical Formula 1)
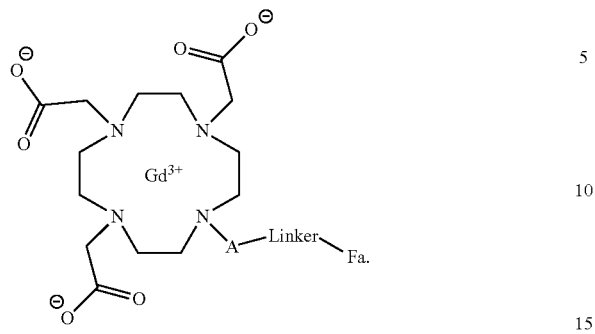
10. The method of claim 9, wherein in the step (a), $L^2$ represents the single bond.
* * * * *